(12) United States Patent
Hallinan

(10) Patent No.: US 6,998,503 B2
(45) Date of Patent: Feb. 14, 2006

(54) CRYSTALLINE SOLID FORM OF (2S,5Z)-2-AMINO-7-(ETHANIMIDOYLAMINO)-2-METHYLHEPT-5-ENOIC ACID

(75) Inventor: E. Ann Hallinan, Evanston, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/646,266

(22) Filed: Aug. 22, 2003

(65) Prior Publication Data

US 2004/0132822 A1 Jul. 8, 2004

Related U.S. Application Data

(60) Provisional application No. 60/405,526, filed on Aug. 23, 2002.

(51) Int. Cl.
*C07C 59/76* (2006.01)

(52) U.S. Cl. ..................................................... 562/460
(58) Field of Classification Search ............... 562/460
See application file for complete search history.

(56) References Cited

U.S. PATENT DOCUMENTS 5,854,251 A 12/1998 Hallinan et al. ............ 514/256
5,945,408 A 8/1999 Webber et al. ............. 514/63

FOREIGN PATENT DOCUMENTS

| WO | WO 93/13055 | 7/1993 |
| WO | WO 95/25717 | 9/1995 |
| WO | WO 02/22562 | 3/2002 |
| WO | WO 02/22562 A1 * | 3/2002 |
| WO | WO 02/076395 A2 * | 10/2002 |

OTHER PUBLICATIONS

McInnes et al; J. Exp. Med; 184; 1519; 1996.
Lundberg et al; Lancet; 344; 1673; 1994.
Hamid et al; Lancet; 342; 1510; 1993.
Harold, Mohr, & Tamm; Helvetica Chimica Acta; 66; 2; 744–754; 1983.

* cited by examiner

*Primary Examiner*—Rita Desai
*Assistant Examiner*—Hector M. Reyes
(74) *Attorney, Agent, or Firm*—Philip B. Polster, II; Charles Ashbrook

(57) ABSTRACT

(2S,5Z)-2-amino-7-(ethanimidoylamino)-2-methylhept-5-enoic acid is crystallized as an anhydrous, stoichiometric 1.5 HCl salt and a scaleable crystallization method is disclosed. The salt form was characterized and the absolute configuration of the chiral center was confirmed as "S". (2S,5Z)-2-amino-7-(ethanimidoylamino)-2-methylhept-5-enoic acid was high melting and appears acceptably non-hygroscopic for use in a pharmaceutical composition.

1 Claim, 6 Drawing Sheets

CRYSTALLINE SOLID FORM OF (2S,5Z)-2-AMINO-7-(ETHANIMIDOYLAMINO)-2-METHYLHEPT-5-ENOIC ACID

The present application claims priority under Title 35, United States Code, §119 of the U.S. Provisional application Ser. No. 60/405,526, filed Aug. 23, 2002.

FIELD OF THE INVENTION

The present invention comprises a novel compound useful in the treatment of disease, and more particularly a novel salt of (2S,5Z)-2-amino-7-(ethanimidoylamino)-2-methylhept-5-enoic acid hydrochloride, and pharmaceutical compositions thereof, for the treatment of conditions involving an inappropriate expression of nitric oxide from the inducible isoform of nitric oxide synthase. (2S,5Z)-2-amino-7-(ethanimidoylamino)-2-methylhept-5-enoic acid is described and claimed in commonly assigned U.S. Ser. No. 09/953,049, filed Sep. 15, 2001, which claims priority to U.S. Provisional Ser. No. 60/232,683, filed Sep. 15, 2000, both herein incorporated by reference. (2S,5Z)-2-amino-7-(ethanimidoylamino)-2-methylhept-5-enoic acid is also described in international publication number WO 02/22562, published Mar. 21, 2002, which is a publication of commonly assigned international patent application PCT/US0128673, filed Sep. 15, 2001 and incorporated herein by reference.

BACKGROUND OF THE INVENTION

Nitric oxide (NO) is a bioactive free radical gas produced by any one of several isoforms of the enzyme nitric oxide synthase (NOS). The physiological activity of what was later identified as NO was initially discovered in the early 1980's when it was found that vascular relaxation caused by acetylcholine is dependent on the presence of the vascular endothelium. The factor derived from the endothelium, then called endothelium-derived relaxing factor (EDRF), that mediates such vascular relaxation is now known to be NO that is generated in the vascular endothelium by one isoform of NOS. The activity of NO as a vasodilator has been known for well over 100 years. In addition, NO is the active species derived from known nitrovasodilators including amylnitrite, and glyceryltrinitrate. Nitric oxide is also an endogenous stimulator of soluble guanylate cyclase (cGMP), and thus stimulates cGMP production. When NOS is inhibited by N-monomethylarginine (L-NMMA), cGMP formation is completely prevented. In addition to endothelium-dependent relaxation, NO is known to be involved in a number of biological actions including cytotoxicity of phagocytic cells and cell-to-cell communication in the central nervous system.

The identification of EDRF as NO coincided with the discovery of a biochemical pathway by which NO is synthesized from the amino acid L-arginine by the enzyme NO synthase. There are at least three types of NO synthase as follows:

(i) a constitutive, Ca++/calmodulin dependent enzyme, located in the brain, that releases NO in response to receptor or physical stimulation;

(ii) a Ca++ independent enzyme, a 130 kD protein, which is induced after activation of vascular smooth muscle, macrophages, endothelial cells, and a number of other cells by endotoxin and cytokines; and (iii) a constitutive, Ca++/calmodulin dependent enzyme, located in the endothelium, that releases NO in response to receptor or physical stimulation.

Once expressed, inducible nitric oxide synthase (hereinafter "iNOS") generates NO continuously for long periods. Clinical studies have shown that NO production and iNOS expression are increased in a variety of chronic inflammatory diseases, such as rheumatoid and osteoarthritis (see, e.g, McInnes I. B. et al., *J. Exp. Med.* 184:1519 (1996)), inflammatory bowel disease (see, e.g, Lundberg J. O. N. et al., *Lancet* 344:1673, (1994)), and asthma (see, e.g., Hamid, Q. et al., *Lancet* 342:1510 (1993)), and iNOS is implicated as a major pathological factor in these chronic inflammatory diseases.

Thus, inhibition of excessive NO production by iNOS is likely to be anti-inflammatory. However, since the production of NO from eNOS and nNOS is involved in normal physiology, it would be desirable for any NOS inhibitor that is used for treating inflammation be selective for iNOS, so that normal physiological modulation of blood pressure by eNOS-generated NO, and non-adrenergic, non-cholinergic neuronal transmission by nNOS-generated NO would remain unaffected.

With all pharmaceutical compounds and compositions, the chemical and physical stability of a drug compound is important in the commercial development of that drug substance. Such stability includes the stability at ambient conditions, especially to mositure and under storage conditions. Elevated stability at different conditions of storage is needed to predict the different possible storage conditions during the lifetime of a commercial product. A stable drug avoids the use of special storage conditions as well as frequent inventory replacement. A drug compound must also be stable during the manufacturing process which often requires milling of the drug to achieve drug material with uniform particle size and surface area. Unstable materials often undergo polymorphic changes. Therefore, any modification of a drug substance which enhances its stability profile provides a meaningful benefit over less stable substances.

Several inhibitors of iNOS have been described, such as, for example, 2S,5Z)-2-amino-7-(ethanimidoylamino)-2-m acid, which is described in commonly assigned international publication number WO 02/22562, published Mar. 21, 2002, which is a publication of international patent application PCT/US0128673, filed Sep. 15, 2001. That compound, however, is an amorphous solid. It would be desirable, therefore, to provide a crystalline solid form of an iNOS inhibitor such as 2S,5Z)-2-amino-7-(ethanimidoylamino)-2-methylhept-5-enoic acid.

SUMMARY OF THE INVENTION

The present invention is directed to a novel crystalline salt of (2S,5Z)-2-amino-7-(ethanimidoylamino)-2-methylhept-5-enoic acid hydrochloride, pharmaceutical compositions, a process for preparing the novel salt compounds, a process for preparing pharmaceutical compositions, and methods of using said novel salt compound and compositions for inhibiting or modulating nitric oxide synthesis in a subject in need of such inhibition or modulation by administering a salt of a compound which preferentially inhibits or modulates the inducible isoform of nitric oxide synthase over the constitutive isoforms of nitric oxide synthase. The present salt compound possesses useful nitric oxide synthase inhibiting activity, and is expected to be useful in the treatment or prophylaxis of a disease or condition in which the synthesis or oversynthesis of nitric oxide forms a contributory part.

Stoichiometrically, a unit cell of the novel salt is two molecules of (2S,5Z)-2-amino-7-(ethanimidoylamino)-2-methylhept-5-enoic acid and three molecules of hydrochloric acid.

The novel salt is characterized by some or all of the following physical measurements: elemental analysis (such as by combustion analysis), melting point and heat of fusion (differential scanning calorimetry and thermogravimetric analysis), refractive indices (polarized light microscopy), x-ray powder diffraction pattern, moisture sorption (for example, DVS moisture balance) and vibrational signature (Raman spectrum).

The present novel salt can be used to treat diseases involving cartilage degeneration, which takes place in certain conditions such as arthritis. Accordingly, conditions in which there is an advantage in inhibiting NO production from L-arginine include arthritic conditions such as rheumatoid arthritis, osteoarthritis, gouty arthritis, juvenile arthritis, septic arthritis, spondyloarthritis, acute rheumatic arthritis, enteropathic arthritis, neuropathic arthritis, and pyogenic arthritis. In addition, NO-induced depression of chondrocyte respiration could modulate matrix loss and secondary cartilage mineralization in arthritis, in particular osteoarthritis.

Other conditions for which the present salt may be useful include chronic or inflammatory bowel disease, cardiovascular ischemia, diabetes, congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia, cerebral ischemia, thrombotic stroke, global ischemia (secondary to cardiac arrest), multiple sclerosis and other central nervous system disorders mediated by NO, for example Parkinson's disease and Alzheimer's disease. Further neurodegenerative disorders in which NO inhibition may be useful include nerve degeneration and/or nerve necrosis in disorders such as hypoxia, hypoglycemia, epilepsy, and in external wounds (such as spinal cord and head injury), hyperbaric oxygen convulsions and toxicity, dementia e.g. pre-senile dementia, and AIDS-related dementia, Sydenham's chorea, Huntingdon's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

The present salt may also be used where nitric oxide inhibition may also play a role in the treatment, such as pain including somatogenic (either nociceptive or neuropathic), both acute and chronic. The present compounds could be used in any situation that a common NSAID or opioid analgesic would traditionally be administered.

Still, other disorders that may be treated by inhibiting NO production with the present salt include opiate tolerance in patients needing protracted opiate analgesics, and benzodiazepine tolerance in patients taking benzodiazepines, and other addictive behavior, for example, nicotine and eating disorders. The present compounds may also be useful as antibacterial agents.

Further conditions in which the present salt may be used to inhibit NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

The present salt may also be useful in the treatment of an ocular condition (such as ocular hypertension retinitis uveitis), systemic lupus erythematosis (SLE), glomerulonephritis, restenosis, inflammatory sequelae of viral infections, acute respiratory distress syndrome (ARDS), oxidant-induced lung injury, IL2 therapy such as in a cancer patient, cachexia, immunosuppression such as in transplant therapy, disorders of gastrointestinal motility, sunburn, eczema, psoriasis, gingivitis, pancreatitis, damage to the gastrointestinal tract resulting from infections, cystic fibrosis, treatment to a dysfunctional immune system such as an adjuvant to short term immunosuppression in organ transplant therapy, induction of labor, adenomatous polyposis, controlling tumor growth, chemotherapy, chemoprevention and bronchitis.

The present invention is also directed to pharmaceutical compositions for the treatment of pain, asthma and other airway disorders, cancer, arthritis, ocular disorders including retinopathies and glaucoma, inflammation related disorders including irritable bowel syndrome, and other disorders in which an excessive production of nitric oxide plays a role, which comprises a therapeutically effective amount of a crystal of (2S,5Z)-2-amino-7-(ethanimidoylamino)-2-methylhept-5-enoic acid hydrochloride together with a pharmaceutically acceptable carrier, diluent or vehicle.

Besides being useful for human treatment, this form is also useful for veterinary treatment of companion animals, exotic animals and farm animals, including mammals, birds, and the like. More preferred animals include horses, dogs, and cats.

DETAILED DESCRIPTION OF THE INVENTION

1. Definitions

Figure 1:
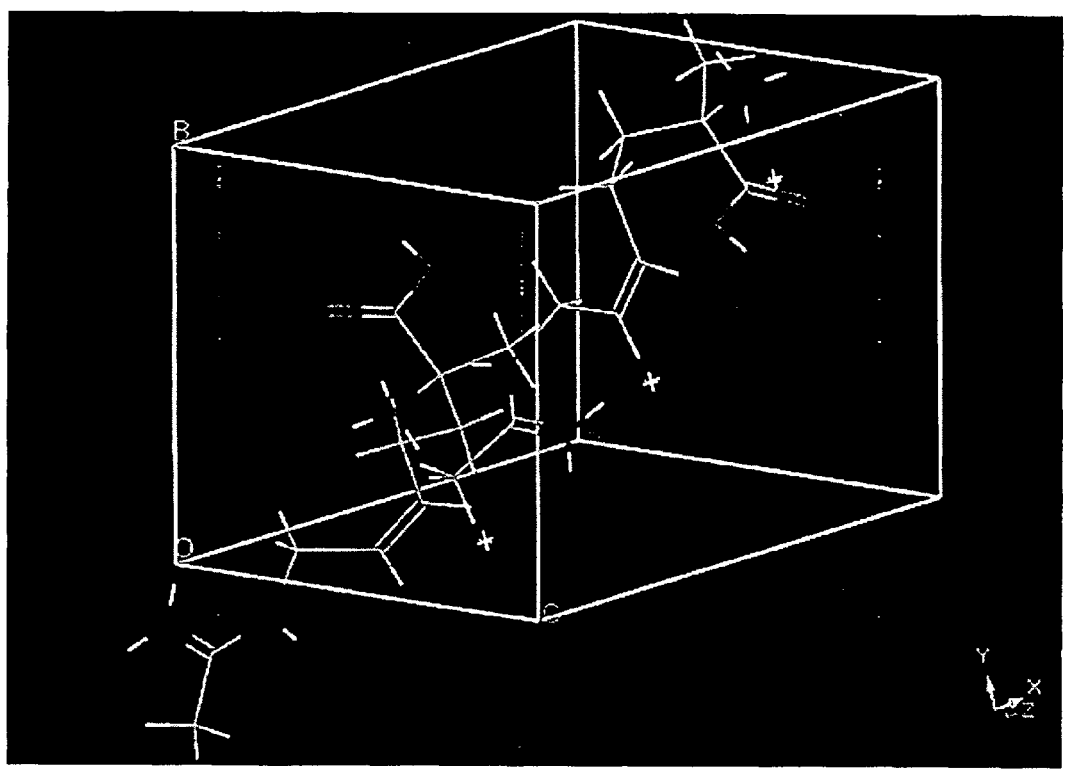
FIG. 1 is a diagram of a unit cell of the 2-amino-7-(ethanimidoylamino)-2-methylhept-5-enoic acid 1.5 HCl crystalline salt of the present invention.

The terms "treat," "treating" and "treatment," as used herein includes prophylactic, palliative treatment, or restorative treatment.

The term "effective amount" means a dose conducive to treatment. An effective amount may be administered in a single dose, or in divided doses over a period of time.

The term "spherulitic" means taking the approximate form of a spherulite.

The term "spherulite" means an ubiquitous form of crystal aggregate, occurring in a wide range of different materials, characterised by radial growth leading to spherical symmetry.

Abbreviations

ACN or alternatively $CH_3CN$ is acetonitrile

AcOH is acetic acid

CH$_2$Cl is methyl chloride
DIBAL is diisobutylaluminum hydride
DMF is dimethylformamide
Et$_3$N is triethylamine
EtOAc is ethyl acetate
KHMDS is potassium hexamethyldisilazide
KOH is potassium hydroxide
MeI methyl Iodide
MS is mass spectrum
MsCl is mesylchloride
NaHCO$_3$ is sodium hydrogen carbonate (sodium bicarbonate)
Na$_2$SO$_4$ is sodium sulphate
THF is tetrahydrofuran Also embraced within this invention is a class of pharmaceutical compositions comprising crystalline (2S,5Z)-2-amino-7-(ethanimidoylamino)-2-methylhept-5-enoic acid hydrochloride in association with one or more non-toxic, pharmaceutically-acceptable carriers and/or diluents and/or adjuvants (collectively referred to herein as "carrier" materials) and, if desired, other active ingredients. The crystalline form of (2S,5Z)-2-amino-7-(ethanimidoylamino)-2-methylhept-5-enoic acid hydrochloride of the present invention may be administered by any suitable route, preferably in the form of a pharmaceutical composition adapted to such a route, and in a dose effective for the treatment intended. The active (2S,5Z)-2-amino-7-(ethanimidoylamino)-2-methylhept-5-enoic acid hydrochloride and compositions may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compound and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

Crystalline (2S,5Z)-2-amino-7-(ethanimidoylamino)-2-methylhept-5-enoic acid hydrochloride can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0–5 to 20%, advantageously 0.5 to 10% and particularly about 1.5% w/w.

For therapeutic purposes, crystalline (2S,5Z)-2-amino-7-(ethanimidoylamino)-2-methylhept-5-enoic acid hydrochloride is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The crystalline Form B may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The amorphous form of (2S,5Z)-2-amino-7-(ethanimidoylamino)-2-methylhept-5-enoic acid hydrochloride may be prepared in accordance with the general scheme shown below:

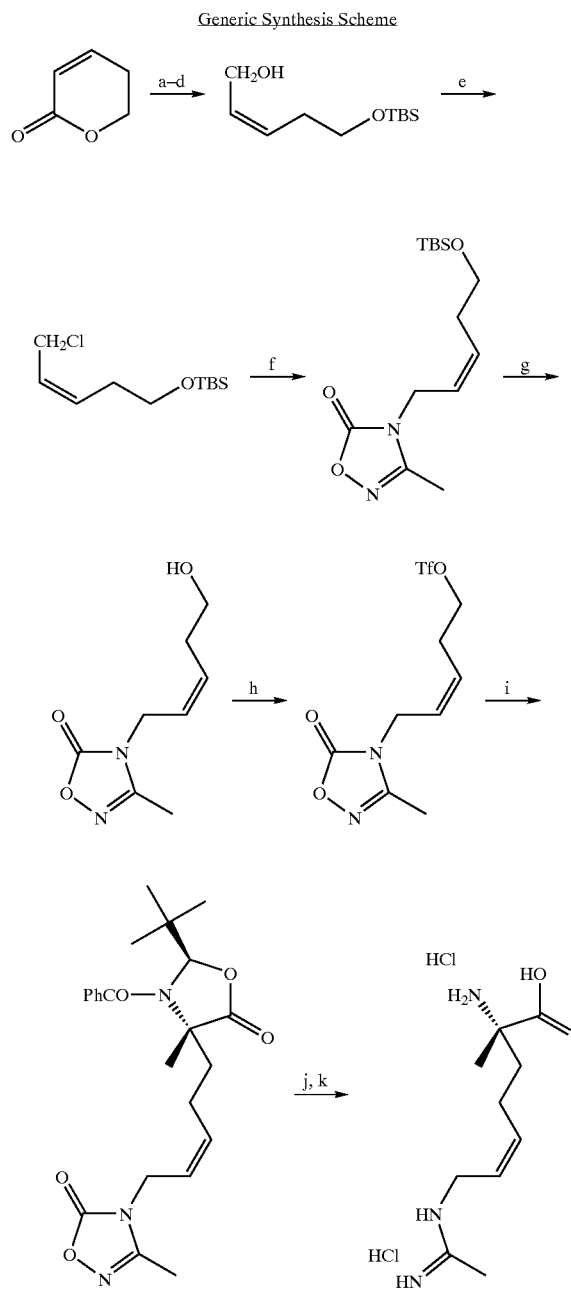

a) KOH
b) MeI
c) TBSCl
d) DIBAL
e) MsCl
f) 3-methyl-1,2,4-oxadiazolin-5-one potassium salt
g) AcOH
h) Tf$_2$O
i) KHMDS/(2S,4S)-3-benzoyl-2-t-butyl-4-methyl-1,3-oxazolidin-5-one
j) Lindlar's catalyst
k) 6 N HCl

EXAMPLE 1

Preparation of (2S,5Z)-2-amino-2-methyl-7-[(1-iminoethyl)amino]-5-heptenoic acid, dihydrochloride:

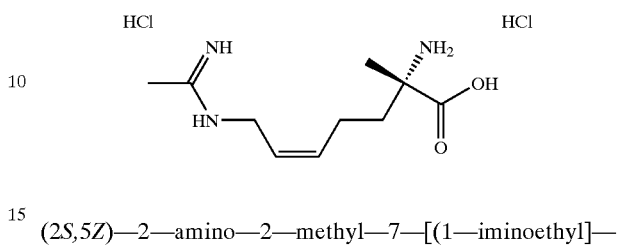

(2S,5Z)—2—amino—2—methyl—7—[(1—iminoethyl]—5—heptenoic acid, dihydrochloride

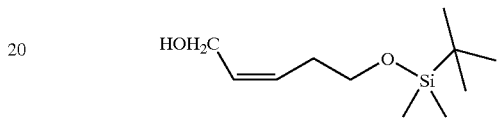

EX-1A) (Z)-5-t-butyldimethylsilyloxy-2-penten-1-ol (EX-1A) was prepared from 5,5-dihydro-2-pyrone (Aldrich) by the method of Harold, Mohr and Tamm *Helvetica Chimica Acta* 66,2, 1983 744–754.

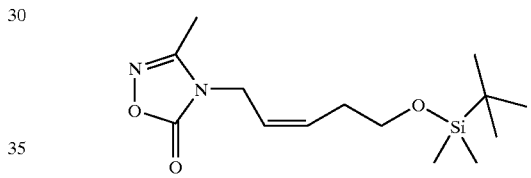

EX-1B) To a solution of EX-1A (720 mg, 3.3 mmol) in CH$_2$Cl$_2$ (25 mL) was added Et$_3$N (525 mg, 5.3 mmol) and methanesulfonyl chloride (561 mg, 4.90 mmol). The reaction mixture was stirred for 15 min at 0° C. then at room temperature for 16 h. Additional CH$_2$Cl$_2$ was added, the solution was extracted with NaHCO$_3$, brine and dried to yield 790 mg of a yellow oil. The oil was dissolved in DMF (20 mL), and (513 mg, 3.7 mmol) was added. The resulting solution was stirred at 50° C. for 16 h. The solvent was removed in vacuo and the residue partitioned between EtOAc and brine. The organic layer was dried (Na2SO4) and concentrated to yield an oil which was purified by flash column chromatography on silica gel eluting with ether:hexane (1:1) to give 780 mg g (79%) of the desired protected Z-allytic cyclic amidine product as a clear oil, that contained only the desired Z-isomer by $^1$HNMR.

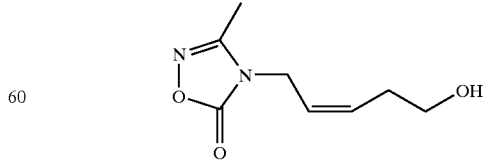

EX-1C) A solution of EX-1B (100 mg, 0.34 mmol) in a mixture of acetic acid (1 mL), THF (3 mL) and water (1 mL) was stirred at room temperature for 16 hours. The resulting solution was concentrated in vacuo to an oil which was disolved in EtOAc. The organic layer was washed with the saturated NaHCO₃, dried (Na₂SO₄), filtered and evaporated to give 80 mg (quant.) of the desired alcohol product as a clear colorless oil.

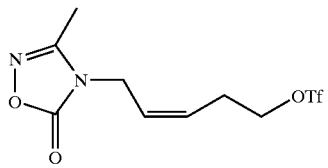

EX-1D) To a CH₂Cl₂ (3 mL) solution of EX-1C (80 mg, 0.43 mmol) was added Et3N (44 mg) and triflic anhydride (146 mg, 0.52 mmol) at 0° C., the mixture was stirred for 1.5 h. The solution was concentrated in vacuo. and To the resulting yellow slurry was added a CH₂Cl₂ (1.5 mL) solution of EX-2D (0.15 g, 0.74 mmol). The crude material was purified by flash column chromatography on silica gel eluting with EtOAc:hexane (1:1) to give 62 mg (44%) of the desired triflate product as a clear oil.

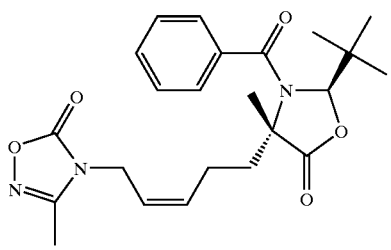

EX-1E) To a THF (10 mL) solution of (2S,4S)-3-benzoyl-2-t-butyl-4-methyl-1,3-oxazolidin-5-one (Ref.) (532 mg, 2.04 mmol) at −78° C. was added KHMDS (4.48 mL, 2.2 mmol, 0.5 M in THF). The resulting orange colored solution was stirred for 15 min. followed by the addition of EX-1D (580 mg, 1.8 mmol). The resulting solution was allowed to warm to room temperature followed by the addition of KHSO₄ (10%, 1.5 mL) brine and EtOAc. The organic layer was separated, dried and concentrated in vacuo to yield 960 mg of a yellow oil. The crude material was purified by flash column chromatography on silica gel eluting with EtOAc:hexane (1:1) to give 138 mg (18%) of the desired alkylated product as a clear oil.

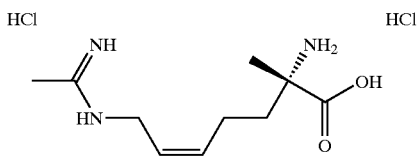

EX-1) To a methanol (10 mL) solution of EX-1E (138 mg, 0.32 mmol) was added Lindlar catalyst (260 mg). The stirred slurry was refluxed for 2 hours, then cooled to room temperature. The catalyst was removed by filtration through celite, and the filtrate was stripped to give the desired deprotected amidine product as a pale yellow oil. A solution of the yellow oil in HCl (6N, 10 mL) was refluxed for 1.75 hours. The solvent was removed in vacuo, and the resulting foam was purified by reverse-phase HPLC eluting with a 30 minute gradient of 0–40% CH₃CN/H₂O (0.25% acetic acid). Fractions containing product were combined and concentrated to a foam. The product was dissolved in 1 $\underline{N}$ HCl and the solvent removed in vacuo (2×) to give 34 mg (20%) of the desired (2S,5Z)-2-amino-2-methyl-7-[(1-iminoethyl)amino]-5-heptenoic acid, dihydrochloride product. MS calcd. for $C_{10}H_{19}N_3O_2$: m/z=214 [M+H]⁺, found: 214. (100%) ¹H NMR (D₂O) δ 1.40 (s, 3H), 1.5–2.0 (m, 4H) 1.90 (s, 3H), 3.55 (m, 2H) 5.15–5.25 (m, vinyl, 1H), 5.30–5.45 (m, vinyl, 1H).

TABLE I

| | Analysis |
|---|---|
| Material Name: | (2S,5Z)-2-amino-7-(ethanimidoylamino)-2-methylhept-5-enoic acid (HCl salt . hydrate) |
| Appearance | colorless to off-colorless glass/gum |
| Identity by LC-MS | conforms to (2S,5Z)-2-amino-7-(ethanimidoylamino)-2-methylhept-5-enoic acid by mass 214 (electrospray+) |
| Assay by LC-MS (by UV) | >99% - contains co-eluting overreduced 2S)-2-amino-7-(ethanimidoylamino)-2-methylheptanoic acid hydrochloride |
| Impurities by LC-MS (by UV) | 2.5% overreduced (2S)-2-amino-7-(ethanimidoylamino)-2-methylheptanoic acid hydrochloride |
| Single other Impurity | (by ratio of MS channel integrals) none detectable conforms to standard |
| dentity by Chiral LC (by UV) | >99.9% chiral purity (S-isomer) |
| Assay by Chiral LC (by UV) | 94.62% chemical purity of(2S,5Z)-2-amino-7-(ethanimidoylamino)-2-methylhept-5-enoic acid 1.73% overreduced (2S)-2-amino-7-(ethanimidoylamino)-2-methylheptanoic acid hydrochloride |

TABLE I-continued

Analysis

| | |
|---|---|
| Single other Impurity by Chiral LC | none detected |
| | conforms to structure of (2S,5Z)-2-amino-7-(ethanimidoylamino)-2-methylhept-5-enoic acid |
| identity by ¹H-NMR (D₂O) | [structure of (2S,5Z)-2-amino-7-(ethanimidoylamino)-2-methylhept-5-enoic acid] |
| Purity by ¹H-NMR (D₂O) | 98% chemical purity of(2S,5Z)-2-amino-7-(ethanimidoylamino)-2-methylhept-5-enoic acid |
| Impurity by ¹H-NMR (D₂O) | 1% of overreduced species (2S)-2-amino-7-(ethanimidoylamino)-2-methylheptanoic acid hydrochloride |
| | [structure of overreduced species] |
| | 1% of bond-migrated species |
| | [structure of bond-migrated species] |
| Residual TFA (%w/w) | not detected (limit of quantitation is 50 ppm) |
| Metal Analysis | Pb < 1 mg/kg |
| | Pd < 2 mg/kg |
| | Ni 1.8 mg/kg |
| | Fe 18.7 mg/kg |
| Elemental Analysis | calc. C: 35.28 H: 7.55 N: 12.34 Cl: 26.03 |
| | found C: 34.97 H: 7.41 N: 12.33 Cl: 24.07 -> 2.5 HCl 2 H₂O |
| | (Note: Material appears to be hygroscopic - elemental analysis reflects water content at time of analysis.) |

EXAMPLE 2 preparation of the crystal form of (2S,5Z)-2-amino-7-(ethanimidoylamino)-2-methylhept-5-enoic acid Crystallization Amorphate (2S,5Z)-2-amino-7-(ethanimidoylamino)-2-methylhept-5-enoic acid, with excess hydrochloride, is freely soluble in water, methanol and ethanol, and soluble in isopropanol and various solvents containing water such as 10% water in THF, water saturated ethyl acetate, 10% water in acetonitrile and higher alcohols with water. The amorphate is insoluble at significantly less than one mg/mL in the dry solvents tested: acetone, MEK, methyl isobutyl ketone, THF, ethyl acetate, chloroform, methylene chloride, hexanes, cylcohexane, di-isopropyl ether, acetonitrile and toluene.

About 460 mg of (2S,5Z)-2-amino-7-(ethanimidoylamino)-2-methylhept-5-enoic acid was dissolved in 10 mL of HPLC grade water. Amberlite IRA400 ion exchange resin that had been converted from the chloride form to the hydroxide form was used to titrate the solution of (2S,5Z)-2-amino-7-(ethanimidoylamino)-2-methylhept-5-enoic acid to pH 10.7. A chloride selective electrode indicated chloride was reduced to 200 ppm. This solution was filtered through a Millipore 5 μm LS membrane and the solution was lyophilized. Elemental analysis of the freeze dried solid, Table II, indicated chloride was reduced to 0.25 equivalents, which was consistent with the 200 ppm ion selective electrode reading.

TABLE II

Elemental analysis results: measured by combustion analysis vs. theory; weight percent.

| Element | Theory 0 HCl | Theory 0.25 HCl | Measured (duplicate) |
|---|---|---|---|
| Carbon | 56.3 | 51.96 | 52.47/52.06 |
| Hydrogen | 8.98 | 8.72 | 8.89/8.96 |
| Nitrogen | 19.7 | 18.18 | 18.16/17.96 |
| Chlorine | 0 | 3.83 | 3.98 |

Hydrochloride salt, (2S,5Z)-2-amino-7-(ethanimidoylamino)-2-methylhept-5-enoic acid was dissolved in water, various low alcohols, THF-water, acetonitrile-water and water saturated ethyl acetate to obtain concentrated solutions. The antisolvents listed above were used to force the salt from solution. Liquid—liquid phase outs, emulsions and glassy precipitates were obtained in all cases. Vapor diffusion cells were also set up with a few systems as well, producing exclusively emulsion phase outs.

A sample of hydrochloride salt was rotary evaporated, dissolved, lyophilized and allowed to stand for four to six weeks in a fume hood. This sample began to spontaneously change. Polarized light microscopy was used to show that crystallization was occurring. Nearly half of the volume of sample became discolored and never did crystallize, but nearly half did crystallize. Some of the material was used as seeds in a number of crystallization experiments, with various solvents, to obtain more crystalline material from (2S,5Z)-2-amino-7-(ethanimidoylamino)-2-methylhept-5-enoic acid hydrochloride. Very little if any crystallization occurred and then only very slowly. Crystals from each lot were examined by polarized light microscopy for evidence of polymorphism. The crystal habit and optical properties remained consistent to one form. Crystals from each lot were biaxial, exhibited a face of high birefringence and a face of low birefringence $n_1-n_2<0.006$, with optic axes emerging from the low birefringence face.

No evidence of solvation was noted by Scanning electron microscopy with energy dispersive spectroscopy SEM/EDS or hot stage polarized light microscopy. The eutectic melt of the crystals; with the discolored oily phase which could not be completely removed without also dissolving the crystals; was about 210° C.

Several large crystals were isolated from a first sample for structural determination. The stoichiometry of the unit cell was determined to be: two independent molecules of (2S,5Z)-2-amino-7-(ethanimidoylamino)-2-methylhept-5-enoic acid and three HCl's. No solvation was observed. The space group was P1 (triclinic) and the unit cell $\alpha$=8.1623, b=9.0524, c=10.5937, alpha=71.522, beta=73.472, gamma=86.086. The absolute configuration of 2-amino-7-(ethanimidoylamino)-2-methylhept-5-enoic acid was confirmed to be "S".

About 1.5 g of (2S,5Z)-2-amino-7-(ethanimidoylamino)-2-methylhept-5-enoic acid, (2.5 HCl×2.0 $H_2O$) was dissolved in 5.0 ml $H_2O$ and amberlite OH resin was added to titrate to pH 7, as measured with a pH electrode and meter. The solution was filtered through a 5 µm LS Millipore filter and lyophilized to yield 903 mg of the monohydrochloride salt. The lyophilized material was virtually dissolved in 6.0 mL of isopropanol containing 0.38% $H_2O$ followed by the addition of HCl (150 µL, 12 M) to form the sesquihydrochloride. This mixture was vortexed and sonicated then allowed to stir overnight at room temperature to ensure saturation and equilibrium. Seed crystals were then added (about 0.1 mg) and stirring continued. Crystallization was noted to begin within minutes and appeared to be substantial within 3 hours. The solution was stirred at room temperature for 48 hours. The crystals were collected by filtration, washed with a small volume of isopropanol and vacuum dried at 40° C. overnight to yield 860 mg, 89% of theory, of white solid.

It will be appreciated that "seeding" a solution of (2S,5Z)-2-amino-7-(ethanimidoylamino)-2-methylhept-5-enoic acid may initiate or increase nucleation under the described conditions. Crystals are available from Pharmacia Corporation, 4901 Searle Parkway, Skokie, Ill., USA 60077.

Two similar experiments were conducted. A few hundred milligrams of (2S,5Z)-2-amino-7-(ethanimidoylamino)-2-methylhept-5-enoic acid were dissolved to approximately the same concentration in isopropanol as the lyophilized material in the previous experiment. The hydrochloride concentration was not adjusted. This system was seeded and stirred at ambient temperature. No crystallization was observed. In the next experiment the pH of the solution was adjusted with concentrated sodium hydroxide to about pH 3 and seeded. Some crystalline product was obtained, but the yield was only about 30 to 40%. Addition of ether increased the yield to near 90%.

EXAMPLE 3 characterization of (2S,5Z)-2-amino-7-(ethanimidoylamino)-2-methylhept-5-enoic acid crystalline salt The solid 2-amino-7-(ethanimidoylamino)-2-methylhept-5-enoic acid 1.5 HCl was crystalline by polarized light microscopy and the crystallite size was on the order of one micrometer. The agglomerated particles were spherulitic. Elemental analysis of 2-amino-7-(ethanimidoylamino)-2-methylhept-5-enoic acid 1.5 HCl by physical methodology provided a very tight correspondence with theory for a 1.5 HCl salt with no solvation, see Table III. Coulometric Karl Fischer water analysis found 0.6% water, 0.09 equivalents, from an average of two measurements.

TABLE III

Elemental analysis results of 2-amino-7-(ethanimidoylamino)-2-methylhept-5-enoic acid 1.5 HCl
Measured by combustion analysis vs. theory; weight percent.

| Element | Measured (duplicate) | Theory 1.5 HCl |
|---|---|---|
| Carbon | 44.56/44.57 | 44.82 |
| Hydrogen | 7.87/7.93 | 7.71 |
| Nitrogen | 15.58/15.60 | 15.68 |
| Chlorine | 19.61/19.68 | 19.85 |

Polarized light microscopy of (2S,5Z)-2-amino-7-(ethanimidoylamino)-2-methylhept-5-enoic acid 1.5 HCl found refractive indices $n_d$ α 1.508, β approximately 1.59, γ 1.608, a negative optic sign and 2V near 37 degrees. Strong dispersion of the optic axes were apparent in the interference figures.

Figure 2:
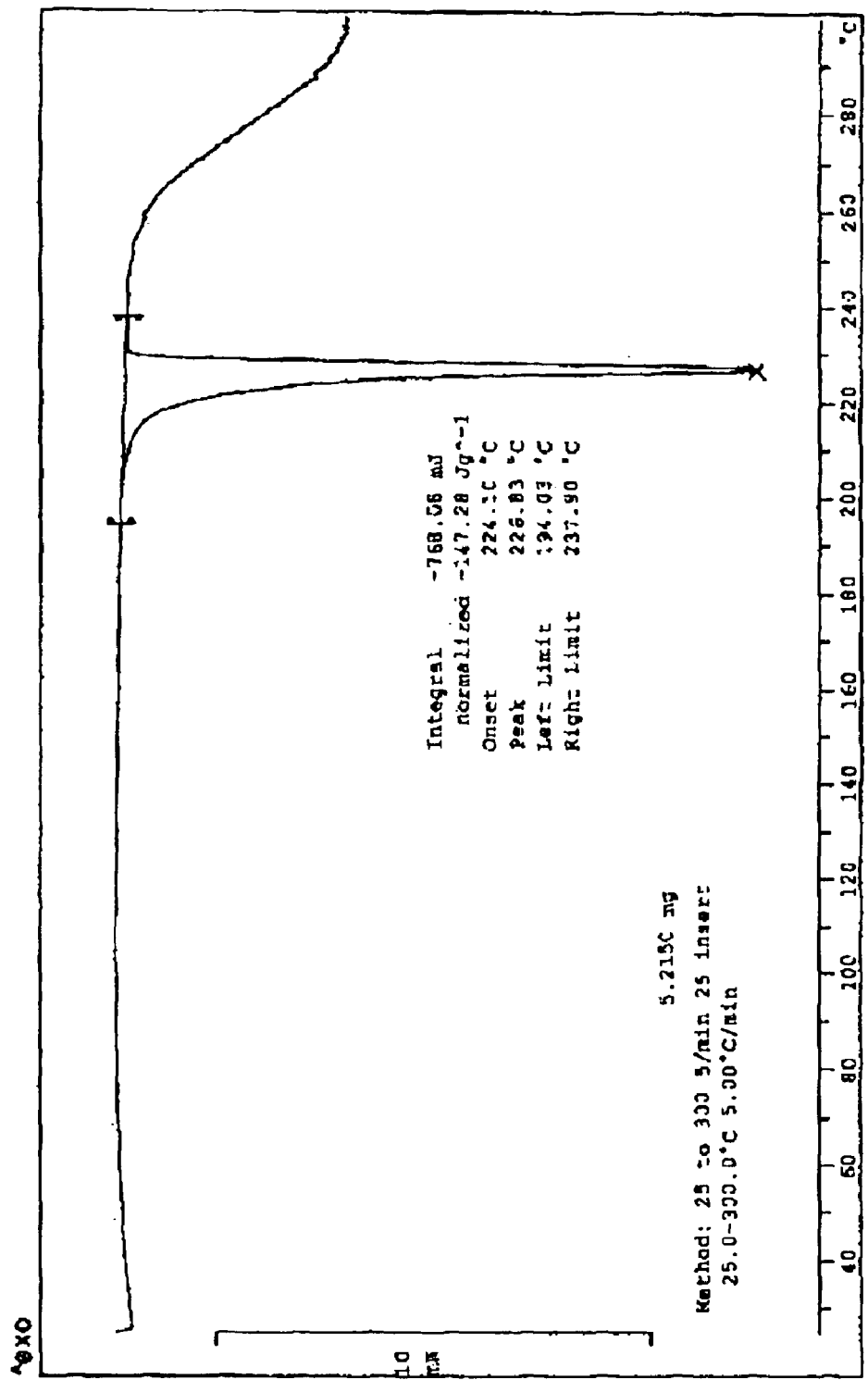
FIG. 2 is a graph of the differential scanning calorimetry study of the 2-amino-7-(ethanimidoylamino)-2-methylhept-5enoic acid 1.5 HCl of the present invention.

Differential scanning calorimetry (DSC) found a single melt at 224° C. and a heat of fusion of 147 joules grams$^{-1}$. (See FIG. 2).

Figure 3:
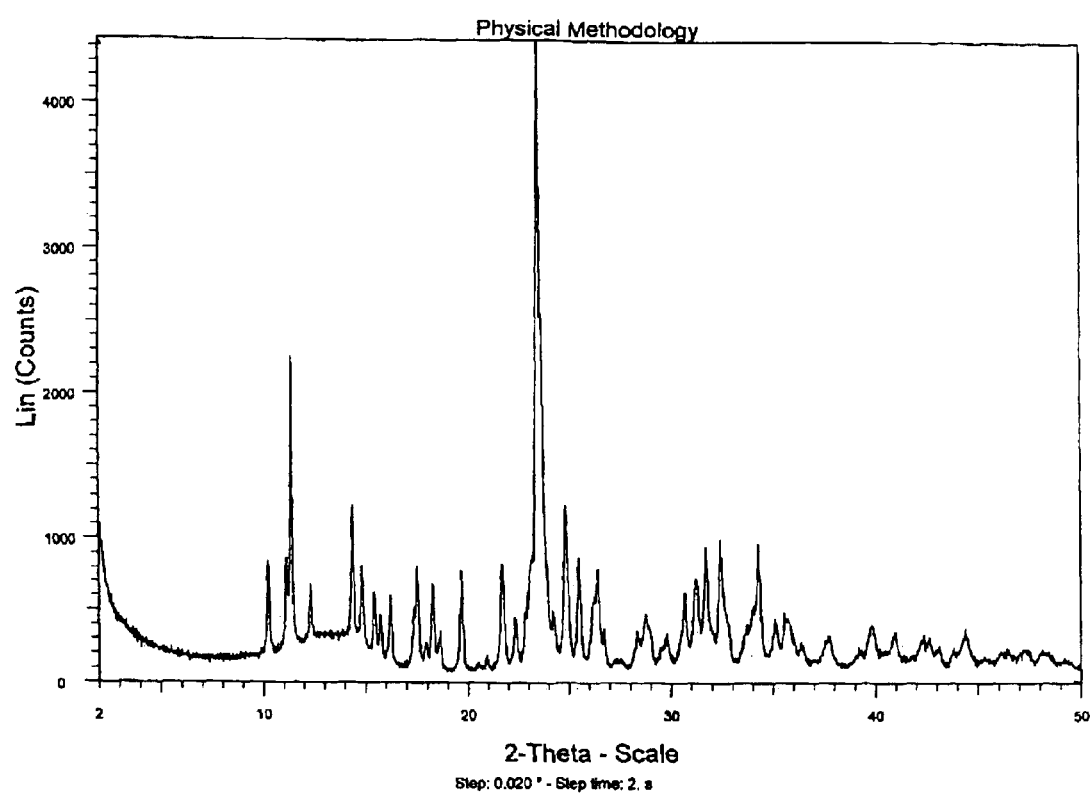
FIG. 3 is a powder X-ray pattern of 2-amino-7-(ethanimidoylamino)-2-methylhept-5-enoic acid 1.5 HCl.

FIG. 3 shows the powder x-ray pattern of 2-amino-7-(ethanimidoylamino)-2-methylhept-5-enoic acid 1.5 HCl.

Figure 4:
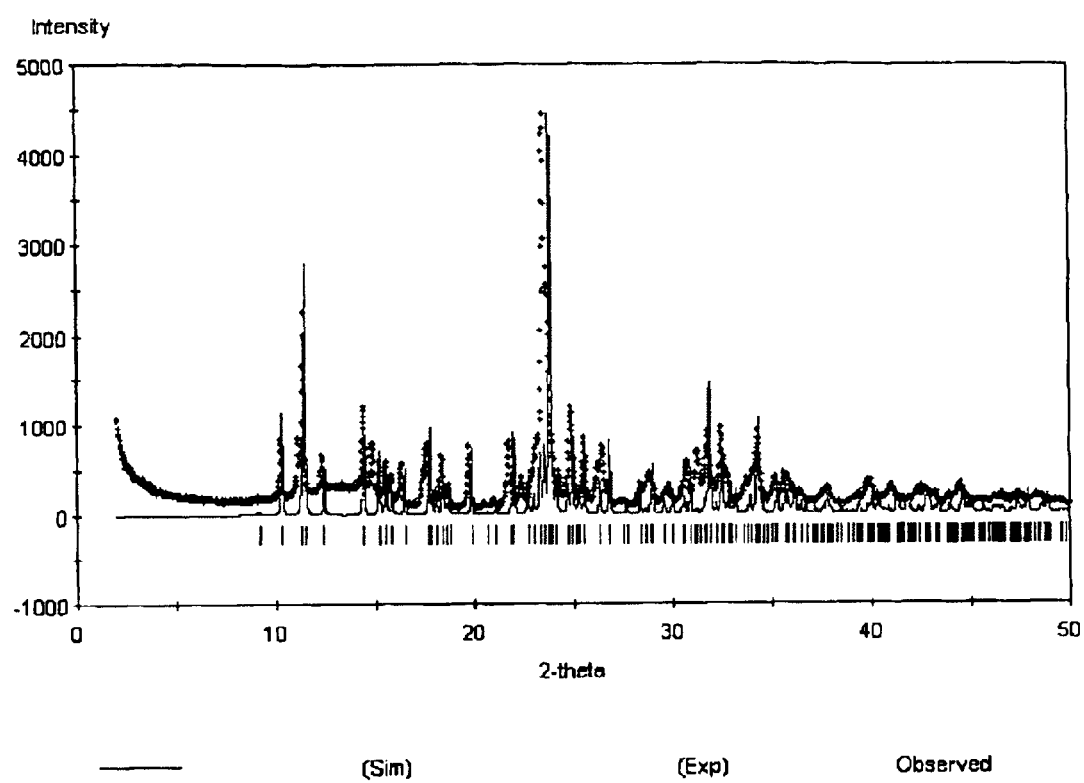
FIG. 4 is the calculated X-ray powder pattern from the single crystal structure overlayed with the powder X-ray pattern of 2-amino-7-(ethanimidoylamino)-2-methylhept-5-enoic acid 1.5 HCl.

Referring to FIG. 4, the calculated x-ray powder pattern from the single crystal structure overlayed with the powder x-ray pattern of 2-amino-7-(ethanimidoylamino)-2-methylhept-5-enoic acid 1.5 HCl agree very well, with allowance for the temperature difference. The single crystal data was collected at 120° K. and the powder x-ray data at ambient.

Figure 5:
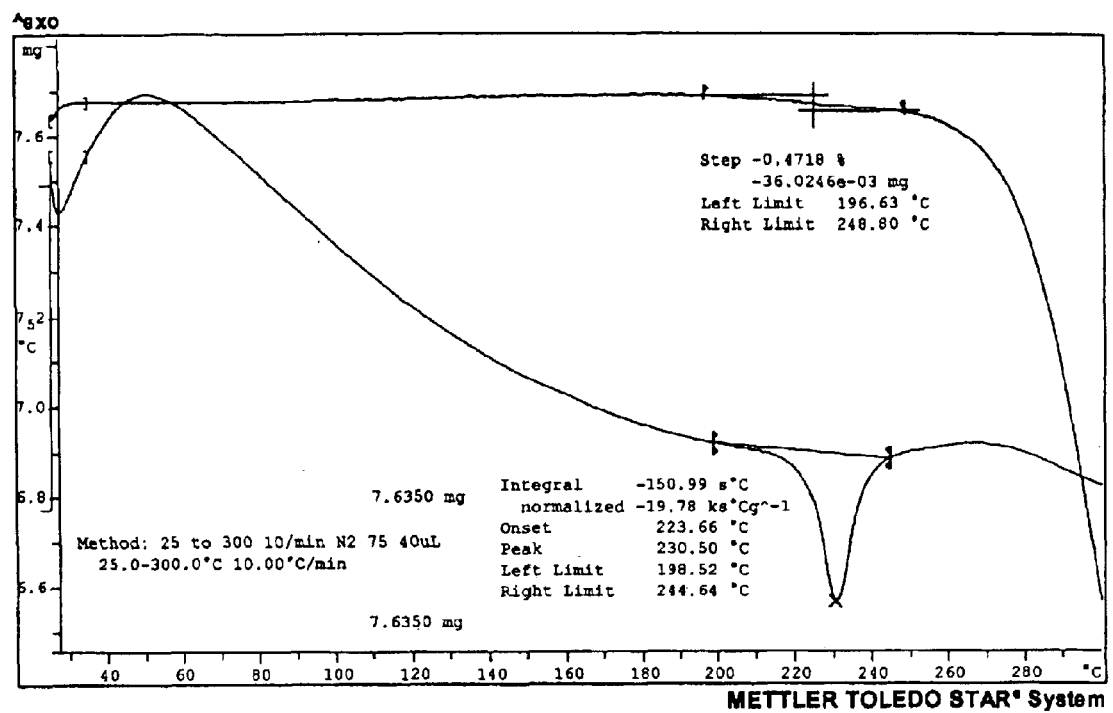
FIG. 5 is a thermogravimetric plot of the -amino-7-(ethanimidoylamino)-2-methylhept-5-enoic acid 1.5 HCl of the present invention.

No mass loss was observed by thermogravimetric analysis (TGA) to the initiation of melt (see FIG. 5). A loss of 0.47% was noted during melting by TGA.

The crystalline 2-amino-7-(ethanimidoylamino)-2-methylhept-5-enoic acid 1.5 HCl is nonhygroscopic at and below 70% relative humidity. Moisture sorption of 2-amino-7-(ethanimidoylamino)-2-methylhept-5-enoic acid 1.5 HCl at 25° C., by DVS moisture balance, showed a moisture gain of 0.91% at 70% relative humidity (R.H.). At 80% R.H. the gain was 18.5%, and at 90% R.H. the gain was 76.8%. The instrument cycled back to low relative humidity and the sample was removed then examined by polarized light microscopy. The sample was fully crystalline after removal from the moisture balance, but the crystallite size had increased. The easily observed optical properties by PLM suggested that no change in crystal form occurred, but at least some of the sample had deliquesced and recrystallized on drying. Table IV shows the detailed data from the DVS moisture balance. This salt form, 1.5 HCl has no solvation.

TABLE IV

| Target RH (%) | Sorption | Desorption | Hysteresis Cycle 1 |
|---:|---:|---:|---:|
| 0.0 | 0.00 | 13.02 | |
| 10.0 | 0.10 | | |
| 20.0 | 0.16 | 18.93 | 18.77 |
| 30.0 | 0.21 | | |
| 40.0 | 0.26 | 22.72 | 22.46 |
| 50.0 | 0.28 | | |
| 60.0 | 0.27 | 33.44 | 33.16 |
| 70.0 | 0.91 | | |
| 80.0 | 18.48 | 67.59 | 49.10 |
| 85.0 | 46.91 | | |
| 90.0 | 76.82 | 76.82 | |

| | | |
|---|---|---:|
| White crystalline solid MP 253 | | |
| H-NMR, HR-MS, CHN | | >99.0 |
| White crystalline solid MP 229.33 | | |
| H-NMR, HR-MS, CHN | | >99.0 |

Figure 6:
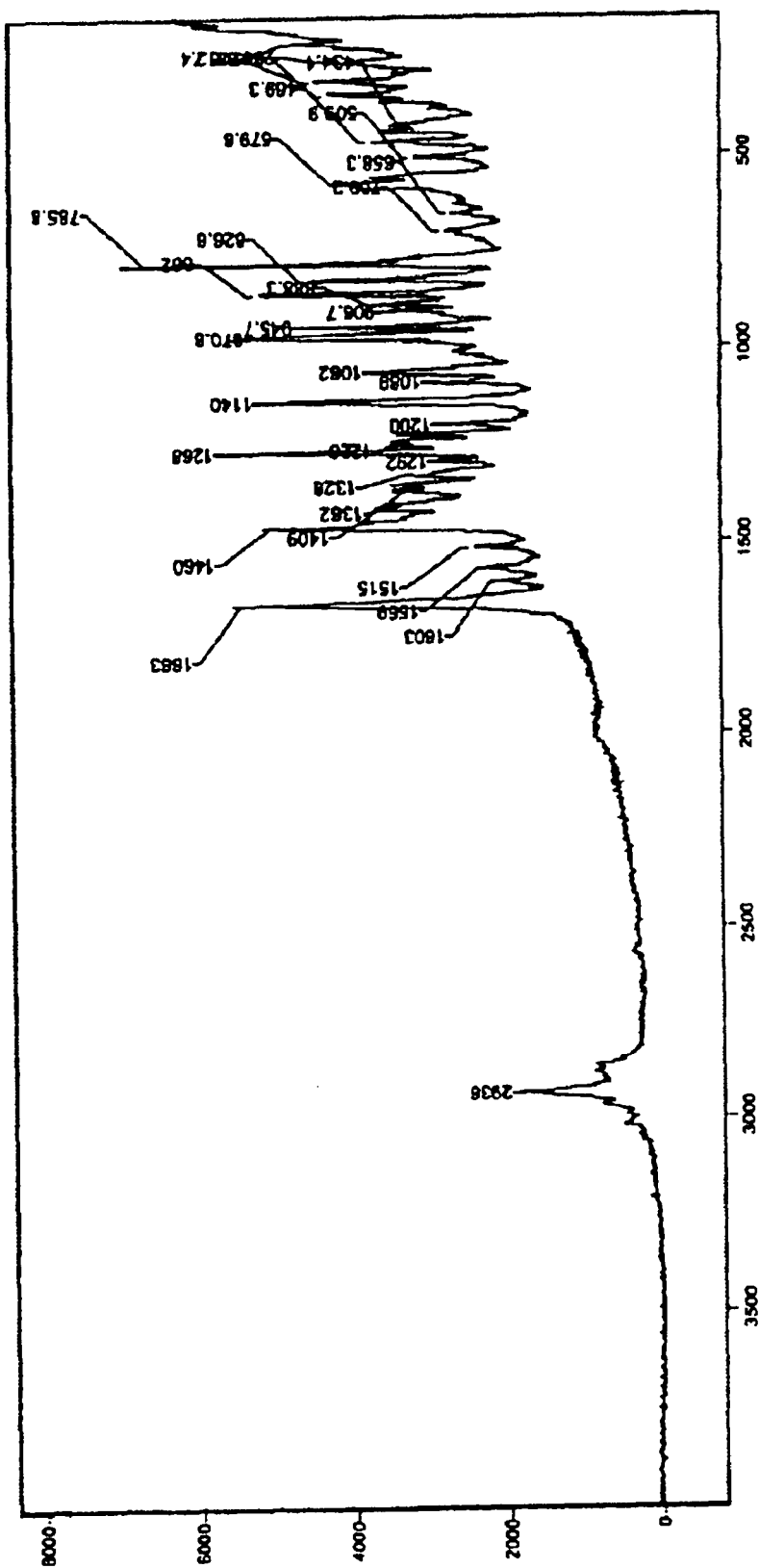
FIG. 6 is the Raman spectrum of the 1.5 HCl salt of (2S,5Z)-2-amino-7-(ethanimidoylamino)-2-methylhept-5-enoic acid of the present invention.

What is claimed is:

1. A crystalline form of 2-amino-7-(ethanimidoylamino)-2-methylhept-5-enoic acid 1.5 hydrochloride characterized by at least one physical measurement selected from the group consisting of: x-ray powder diffraction pattern as shown in FIG. 3, Raman spectrum as shown in FIG. 6, melting point of 224° C. and a heat of fusion of 147 joules gram$^{-1}$.

* * * * *